United States Patent [19]
Bird

[11] 4,039,139
[45] Aug. 2, 1977

[54] VENTILATOR AND METHOD

[76] Inventor: Forrest M. Bird, 212 NW. Cerritors, Palm Springs, Calif. 92262

[21] Appl. No.: 591,708

[22] Filed: June 30, 1975

Related U.S. Application Data

[62] Division of Ser. No. 499,554, Aug. 22, 1974, Pat. No. 3,915,164.

[51] Int. Cl.² .............................................. F16K 15/18
[52] U.S. Cl. .............................. 251/65; 137/DIG. 2; 251/61; 251/75; 251/82; 137/853; 137/854
[58] Field of Search ..................... 251/65, 82, 83, 61, 251/75; 137/DIG. 2, 853, 854

[56] References Cited

U.S. PATENT DOCUMENTS

| | | | |
|---|---|---|---|
| 972,752 | 10/1910 | Cowper-Smith | 251/61 |
| 1,568,522 | 1/1926 | Mitterreiter | 137/DIG. 2 |
| 2,293,068 | 8/1942 | McLaughlin | 251/61 |
| 2,644,477 | 7/1953 | King | 251/65 X |
| 3,013,531 | 12/1961 | Mueller et al. | 251/65 X |
| 3,282,293 | 11/1966 | Barger | 137/614.19 |
| 3,407,827 | 10/1968 | Follett | 251/65 X |

*Primary Examiner*—Arnold Rosenthal
*Attorney, Agent, or Firm*—Flehr, Hohbach, Test, Albritton & Herbert

[57] ABSTRACT

Ventilator with an inhalation phase and an exhalation phase in its operative cycle having a servo controller with an inlet adapted to be connected to supply gas under pressure and also having an outlet. The controller has control valve means movable between open and closed positions to control the flow of gas from the inlet to the outlet of the servo controller. The control valve means is an open position during the inhalation phase of the ventilator and in a closed position in the exhalation phase of the ventilator. Means is provided for supplying gases to the patient from the servo controller until a predetermined pressure has been reached. After the predetermined pressure is reached, means is provided to supply an additional flow of gases to the patient to provide an inspiratory apneustic plateau for the patient. After a predetermined period of time, the patient is permitted to exhale and thereafter the same cycle is repeated.

3 Claims, 17 Drawing Figures

FIG_5

FIG_6    FIG_15

FIG_16

FIG-17

VENTILATOR AND METHOD

CROSS REFERENCE TO RELATED APPLICATION

This application is a division of application Ser. No 499,554 filed Aug. 22, 1974, now U.S. Pat. No. 3,915,164.

BACKGROUND OF THE INVENTION

Various ventilator and respirators have been provided. However, they have been deficient in that they have failed to provide an adjustable post-inspiratory flow. In the past, when post-inspiratory flow was developed by locking up the proximal airway in a static state, many subjects developed varying degrees of dyspnea. There is, therefore, a need for a new and improved ventilator and method which provides an adjustable post-inspiratory apneustic plateau flow for a period of time which does not have the above named disadvantages.

SUMMARY OF THE INVENTION AND OBJECTS

The ventilator has an inhalation phase and an exhalation phase in its operative cycle. A servo controller is provided having an inlet adapted to be connected to a supply of gas under pressure. The controller also has an outlet and control valve means disposed in the controller and movable between open and closed positions to control the flow of gas from the inlet to the outlet. The control valve means is in an open position during the inhalation phase of the ventilator and in a closed position during the exhalation phase of the ventilator. A patient adapter is provided. Means is also provided for supplying gas from the outlet of the servo controller to the patient adapter. Exhalation valve means is provided which is associated with the patient adapter and is movable between open and closed positions to permit exhalation by the patient during the exhalation phase. Means is provided for supplying gas from the outlet to the exhalation means to maintain it in a closed position during the time gas is being supplied from the outlet. Means is provided for sensing the pressure of the gas in the means for supplying gas from the outlet of the controller to the patient adapter and for switching the controller from an open to a closed position when a predetermined pressure has been reached. Apneustic plateau valve means is provided having an inlet and an outlet. A valve member is provided in the valve means movable between open and closed positions to control the flow of gas from the inlet to the outlet. Diaphragm operated means is provided for moving the valve member between open and closed positions. Means is provided for supplying gas from the outlet of the controller to the diaphragm operated means and to the patient adapter. The means for supplying gas including valve means for controlling the flow of fluid from the diaphragm operated means whereby after the servo controller is switched to a closed position an additional flow of gas is supplied to the patient adapter for a predetermined period of time to thereby enhance the volume of gas and distribution of gas in the patient's lungs while maintaining a graded topping-off pressure dependent upon the pulmonary compliance of the patient's lungs.

In general, it is an object of the present invention to provide a ventilator and method which has means for providing an adjustable additional flow of gas to the patient after the major portion of the inspiration phase has been completed.

Another object of the invention is to provide a ventilator and method of the above character in which the additional flow of gases enhances the volume of gas and the distribution of gas in the patient's lungs.

Another object of the invention is to provide a ventilator and method of the above character in which a graded topping-off pressure dependent upon the pulmonary compliance of the patient's lungs is provided during the time of the additional flow of gas to the patient.

Another object of the invention is to provide a ventilator of the above character which is relatively simple in construction and which can be readily cleaned.

Another object of the invention is to provide a ventilator of the above character which can be readily used by a patient.

Additional objects and features of the invention will appear from the following description in which the preferred embodiment is set forth in detail in conjunction with the accompanying drawings.

DESCRIPTION OF THE PREFERRED EMBODIMENT

Figure 1:
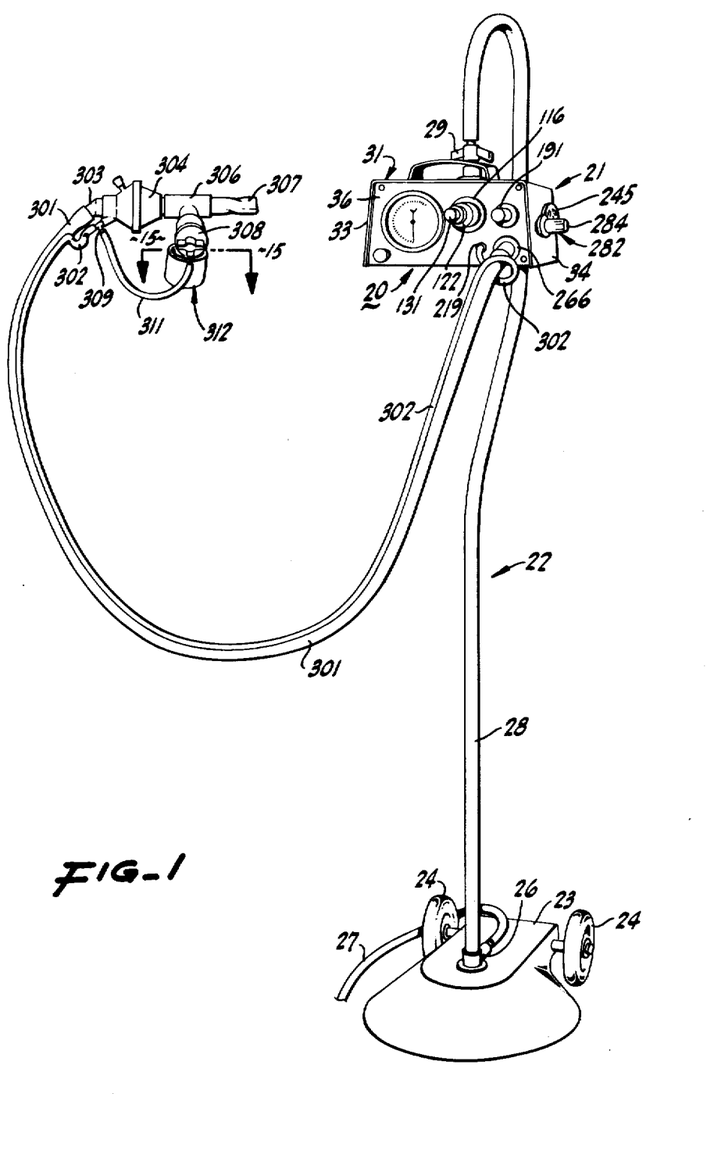
FIG. 1 is a perspective view of a ventilator incorporating the present invention.
Figure 2:
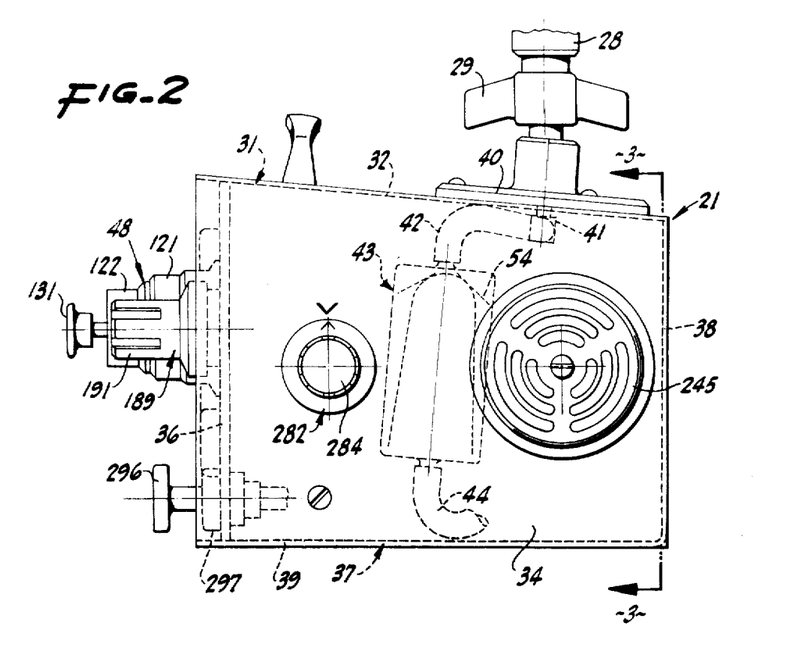
FIG. 2 is a side elevational view of a portion of the ventilator shown in FIG. 1.
Figure 3:
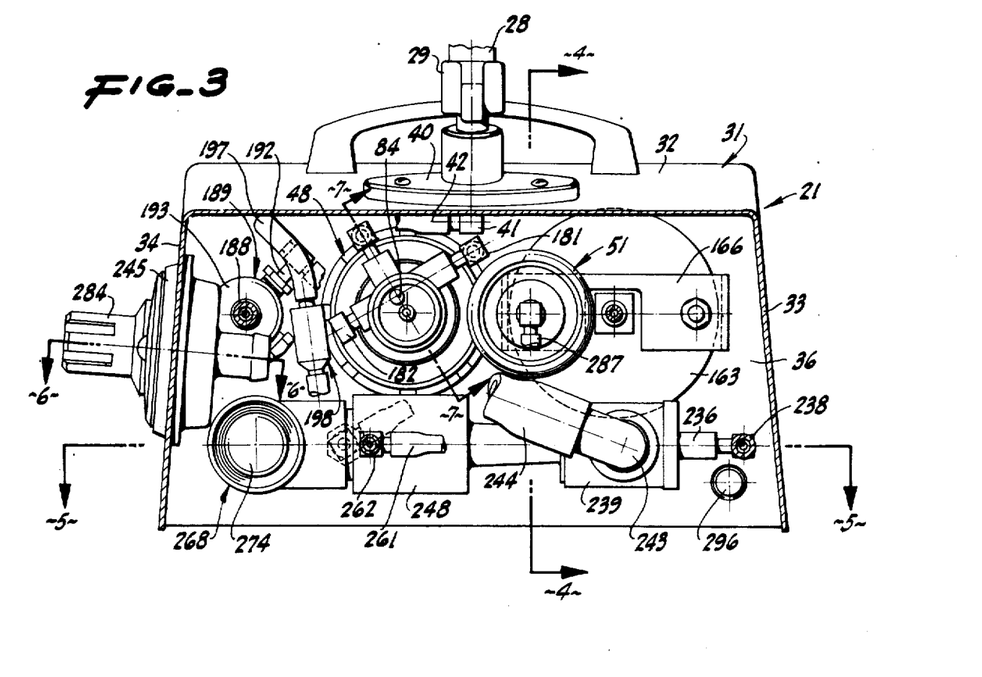
FIG. 3 is a cross-sectional view taken along the line 3—3 of FIG. 2.

The ventilator 20 incorporating the present invention consists of a cabinet or case 21 which is supported in a suitable manner such as by a stand 22. The stand 22 is of a conventional type and consists of a base 23 which is provided with a pair of wheels 24 so that it can be readily moved from one location to another. A fitting 26 is mounted on the base 23 and is connected to a suitable supply of a gas through a tube 27 for the ventilator such as a supply of oxygen which is connected to the tube 27. The gas is supplied from the fitting 26 through an upright tubular member 28 which is mounted within the fitting and which has its upper end bent into a U with the extremity of the same connected to a wing-type connector 29. The connector 29 can be connected to an oxygen blender (not shown) of the type described in U.S. Pat. No. 3,727,627. Alternatively, it can be connected directly to the ventilator 20 as shown in FIG. 1.

The cabinet or case 21 consists of a U-shaped member 31 formed of sheet metal which is provided with a top wall 32 and side walls 33 and 34. It also consists of a front wall or panel 36 and an L-shaped member 37 which forms the rear wall 38 and a bottom wall 39. As can be seen, the cabinet is generally a rectangular six-sided enclosure. A flanged boss 40 is mounted on the top wall 32 of the cabinet and is connected to the wing nut connector 29. A fitting 41 is mounted in the flange boss 40 and is connected by a tube 42 to one end of a filter 43. Gas is supplied from the source at a pressure ranging from approximately 45 to 75 p.s.i. and preferably about 50 p.s.i. A tube 44 connects the other end of the filter 43 to a tee 46 and one end of the tee is connected by a tube 47 to the inlet of a sequencing servo cartridge or controller 48 and the other end of the tee 46 by a tube 49 to the inlet of an apneustic plateau cartridge 51. The sequencing servo cartridge or controller 48 is generally of the type described in U.S. Pat. No. 3,753,436. The filter 43 is in the form of a cylindrical cartridge which is sealed at both ends and which has a filter member 53 formed of a suitable filter material such as nylon mesh which is generally cup-shaped in form and which has its lower extremity supported by triangular supports 54 formed integral with the cartridge.

Figure 7:
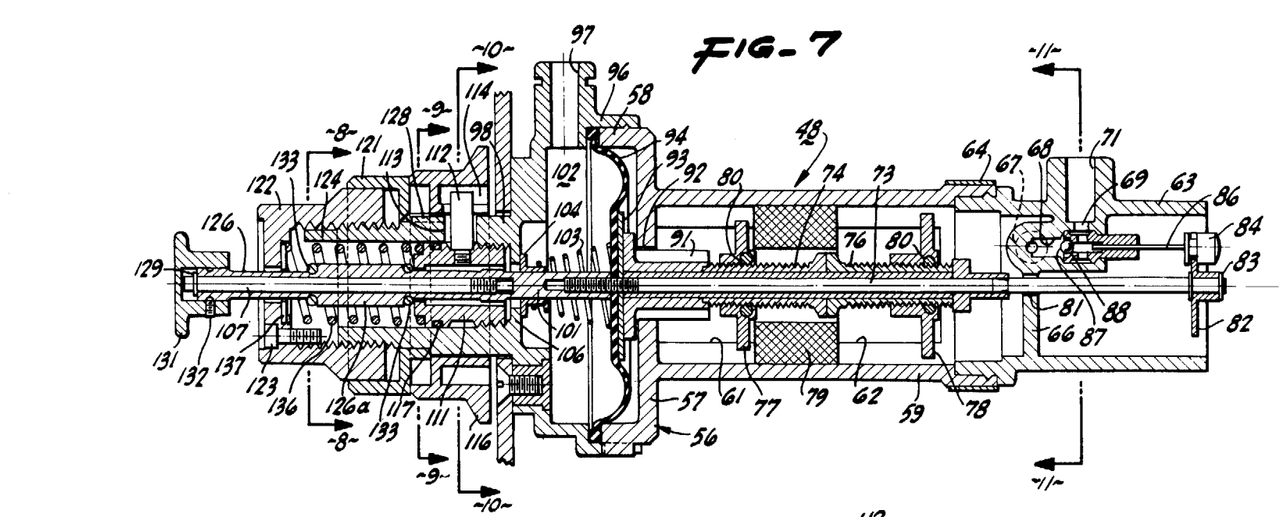
FIG. 7 is an enlarged cross-sectional view of the servo controller utilized in the ventilator.
Figure 8:
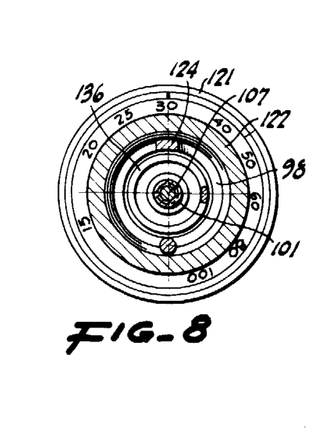
FIG. 8 is a cross-sectional view taken along the line 8—8 of FIG. 7.
Figures 9, 10:
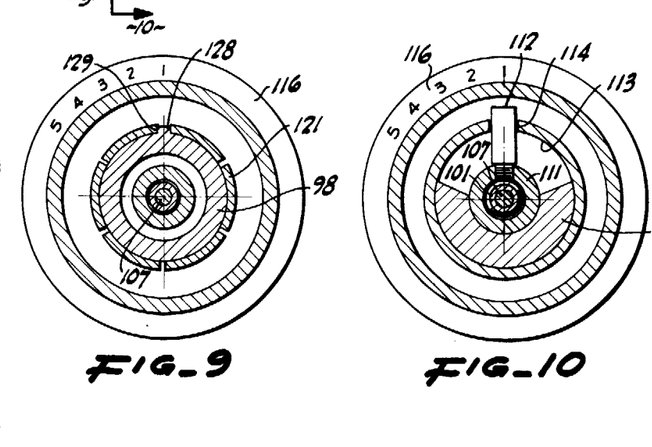
FIG. 9 is a cross-sectional view taken along the line 9—9 of FIG. 7.
FIG. 10 is a cross-sectional view taken along the line 10—10 of FIG. 7.
Figure 11:
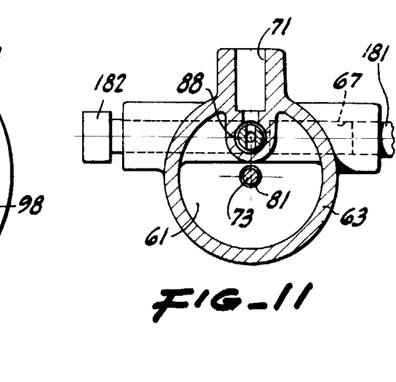
FIG. 11 is a cross-sectional view taken along the line 11—11 of FIG. 7.

The sequencing servo cartridge 48 consists of a housing 56 formed of a suitable material such as plastic. The housing 56 is provided with a circular flat bottom wall 57 which has a rim 58 formed integral therewith and extending outwardly at right angles from the bottom wall. The housing 56 is also provided with a cylindrical extension 59 formed integral therewith which extends outwardly from the flat bottom wall 57 and in a direction opposite the rim 58. The hollow cylindrical extension 59 is provided with pairs of spaced opposing openings 61 and 62. A hollow cylindrical control body 63 formed of a suitable material such as transparent plastic has one end mounted within the outer extremity of the cylindrical extension 59 and is retained therein by a metal retaining ring 64 which slides over the outer extremity of the cylindrical extension 59 after the control body 63 is mounted therein. The control body is provided with a wall 66 which extends diametrically across the control body. The control body 63 is formed to provide a flow passage 67 which serves as a pressure inlet port 68 normally in communication with a passage 69 opening into an outlet port 71.

A master shaft 73 is slidably mounted in the housing 56. The master shaft 73 is formed of a suitable material such as steel. A pair of sleeve-like parts 74 and 76 formed of a suitable material such as plastic are mounted on the master shaft 73 so that they are in engagement with each other. The exteriors of the bushings 74 and 76 are threaded and have threadedly mounted thereon a magnetic starting effort armature 77 and a magnetic pressure armature 78. The plastic parts 74 and 76 are provided with teeth which engage each other so that the two parts will not rotate with respect to each other. The armatures 77 and 78 are adapted to be attracted by a cylindrical magnet 79 mounted within the cylindrical extension 59 of the housing 56 between the openings 61 and 62. The starting effort armature 77 and the pressure armature 78 can be adjusted longitudinally of the master shaft 73 by rotating the same on the bushings 74 and 76 to increase or decrease the force applied to each of the armatures by the magnet 79. O-rings 80 are provided between the armatures 77 and 78 and the bushings 74 and 76 to provide a desired amount of friction.

The master shaft 73 extends through a hole 81 provided in the wall 66 of the control body 63. A circular servo plate 82 is mounted on the outer extremity of one end of the master shaft 73 and is retained in this position by snap rings 83. A fitting 84 is mounted in the servo plate 82 adjacent the outer margin of the same and carries a servo plunger 86. The servo plunger 86 is adapted to engage a ball 87 that serves as a valve member which is adapted to engage an annular valve seat 88 whereby flow passages between the inlet port 68 and the outlet port 71 can be established or interrupted depending upon the position of the ball 87.

An anti-rotation hub 91 which is rectangular in cross-section is mounted upon the master shaft 73 and is mounted in an opening 92 provided in the flat bottom wall 57 to prevent rotation of the master shaft. A metal plate 93 is mounted on the shaft and supports the inner margin of a flexible diaphragm 94. The outer margin of the diaphragm 94 is clamped between the rim 58 and the pressure bell 96. The anti-rotational hub 91 prevents possible "wind up" of the diaphragm 94 and splints the backside of the diaphragm 94. The pressure bell 96 is frictionally retained on the housing 56 by a cooperating ridge and groove (not shown) and is provided with a sensing port 97. The pressure bell is provided with a cylindrical extension or hub 98 formed integral therewith. An accessory shaft hub 101 is threaded onto the master shaft and extends into the extension 98 of the pressure bell 96. A pressure chamber 102 is formed within the pressure bell and is in communication with the sensing port 97. Yieldable means in the form of a helical spring 103 is provided within the chamber 102 which has one end engaging the diaphragm 94 and has the other end engaging a flanged sleeve 104 slidably mounted on the accessory shaft hub 101. The flanged sleeve 104 engages a wall 106 formed in the extension 98. An accessory shaft 107 has one end threaded into the accessory shaft hub 101 and extends axially of the extension 98.

An adjustable sensitivity stop member 111 is threadedly mounted within the interior of the extension 98 and can be moved axially of the accessory shaft 107 by rotation of the same through the limiting screw 112 threaded into the adjustable sensitivity stop member 111 and extends through a slot 113 provided in extension or hub 98. The limiting screw 112 extends into a slot 114 provided in a sensitivity control dial 116 which is used for rotating the adjustable sensitivity stop member 111. O-ring 117 provides friction between the member 111 and the interior of the extension 98 and with the screw 112 holding the dial 116 in place.

An index hub 121 is mounted upon the extension 98. An adjustable pressure limiting knob 122 is mounted within the index hub 121. The pressure limiting knob 122 is threadedly mounted on the exterior of the extension 98. It is provided with a pin 123 extending inwardly which is adapted to engage an abutment 124 provided on the extension 98 to limit the rotation of the knob 122. The pressure limiting knob 122 and the sensitivity control knob 116 serve as a compound knob for operation of the servo cartridge 48.

A cam shaft 126 is mounted on the accessory shaft 107 and is retained thereon by a retaining ring 127. A key 128 is formed integral with the extension 98 and engages a wide slot 129 provided in the index hub 121.

A manual override knob 131 is secured to the cam shaft 126 by a set screw 132. The cam shaft 126 is provided with an enlarged cylindrical portion 126a which has O-rings 133 mounted thereon that serve as bumpers. A helical drag spring 136 is mounted within the extension 98 and has one end engaging the adjustable sensitivity stop member 111 and has the other end engaging an inner surface of the knob 122. A flat washer 137 is provided between 136 spring and 122 knob to add friction to inhibit rotation of the pressure limiting knob 122. The drag spring 136 performs two functions. One is providing indirect friction for the starting effort dial or knob 116 and direct function for the pressure limiting knob 122. The other is eliminating possible backlash in the coarse threads of both travel limiting stops for the knobs 116 and 122 by maintaining tension between the stops.

Figure 12:
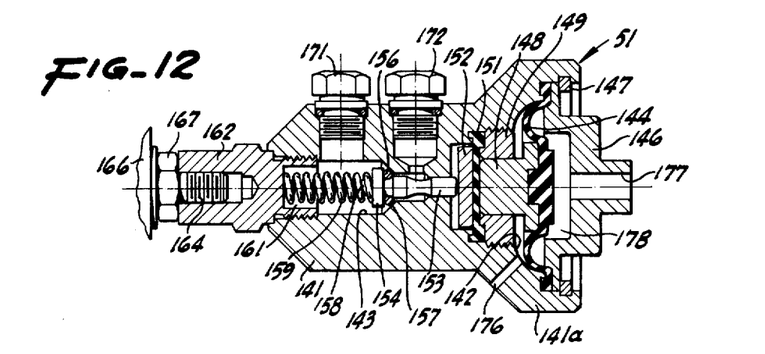
FIG. 12 is a cross-sectional view of the normally closed apneustic control cartridge.

The apneustic control cartridge 51 is shown in detail in FIG. 12, and as shown therein, consists of housing 141 which is provided with an enlarged portion 141a. The portion 141a has a cup-shaped cavity 142 which is in communication with a bore 143 extending longitudinally of the housing. A flexible diaphragm 144 is disposed within the cavity 142 and has its outer margin clamped between the enlarged portion 141a and an end or retainer cap 146 which is retained witin the enlarged portion 141a by a retaining ring 147. A rigid cam button 148 engages a central portion of the diaphragm 144 and extends through a seal retainer 149 threaded into the enlarged portion 141a. A flexible sealing member 151 has its outer margin engaged between the retainer 149 and the interior of the housing 141. One side of the sealing ring 151 is engaged by the button 148 and the other side engages a rigid disc or button 152. The button 152 engages a valve stem 153 forming a part of a valve member or puppet valve 154 which carries an O-ring 156 adapted to make sealing engagement with a valve seat 157 formed on the interior of the housing 141. The valve member 154 is provided with a boss 158 in which there is mounted one end of helical coil spring 159 extending axially of the bore 143. The other end of the spring 159 is seated in a well 161 of a fitting or mounting cap 162 threaded into the end of the housing 141.

A pressure gauge 163 is mounted on the front panel 36 by a screw 164 which is part of the gauge 163 and extends through a U-shaped bracket 166 mounted on the front panel 36 and is secured thereto by a nut 167. The cartridge 51 is mounted on the outer extremity of the screw 164 by threading the mounting cap 162 upon the screw 163.

First and second fittings 171 and 172 with fitting 171 being the inlet fitting and fitting 172 being the outlet fitting are threaded into the body 141 and are in communication with the bore 143 on opposite sides of the valve seat 157. A bleed hole 176 is provided in the housing 141 and serves to prevent any build-up of pressure against the diaphragm which could give a false indication. The end cap 146 is provided with a servo port 177 which is in communication with a chamber 178 provided on one side of the diaphragm 144.

The tube 47 is connected to a fitting 181 which is mounted in one end of the means forming the flow passage 67. The other end is closed by a plug 182. The outlet port 71 has a fitting 183 mounted therein which is connected to a tube 184. The tube 184 is connected to a tee 186. One end of the tee 186 is connected by tube 187 which is connected to a fitting 188 mounted in a flow rate valve 189 of the conventional type. The flow rate valve is provided with a control knob 191 for adjusting the rate of flow of gas through the flow rate control valve 189 through a fitting 192 which is mounted in the body 193 of the valve. The fitting 192 is connected by a tube 194 to a tee 196. One end of the tee 196 is connected by a tube 197 to a check valve assembly 198.

Figure 13:
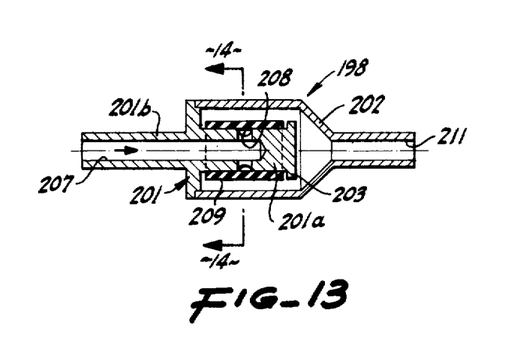
FIG. 13 is a cross-sectional view taken along the line 13—13 of FIG. 5.
Figure 14:
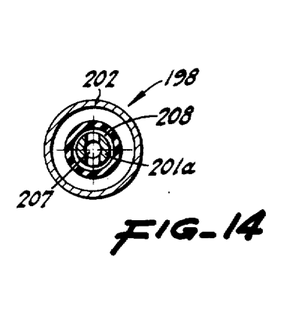
FIG. 14 is a cross-sectional view taken along the line 14—14 of FIG. 13.
Figure 17:
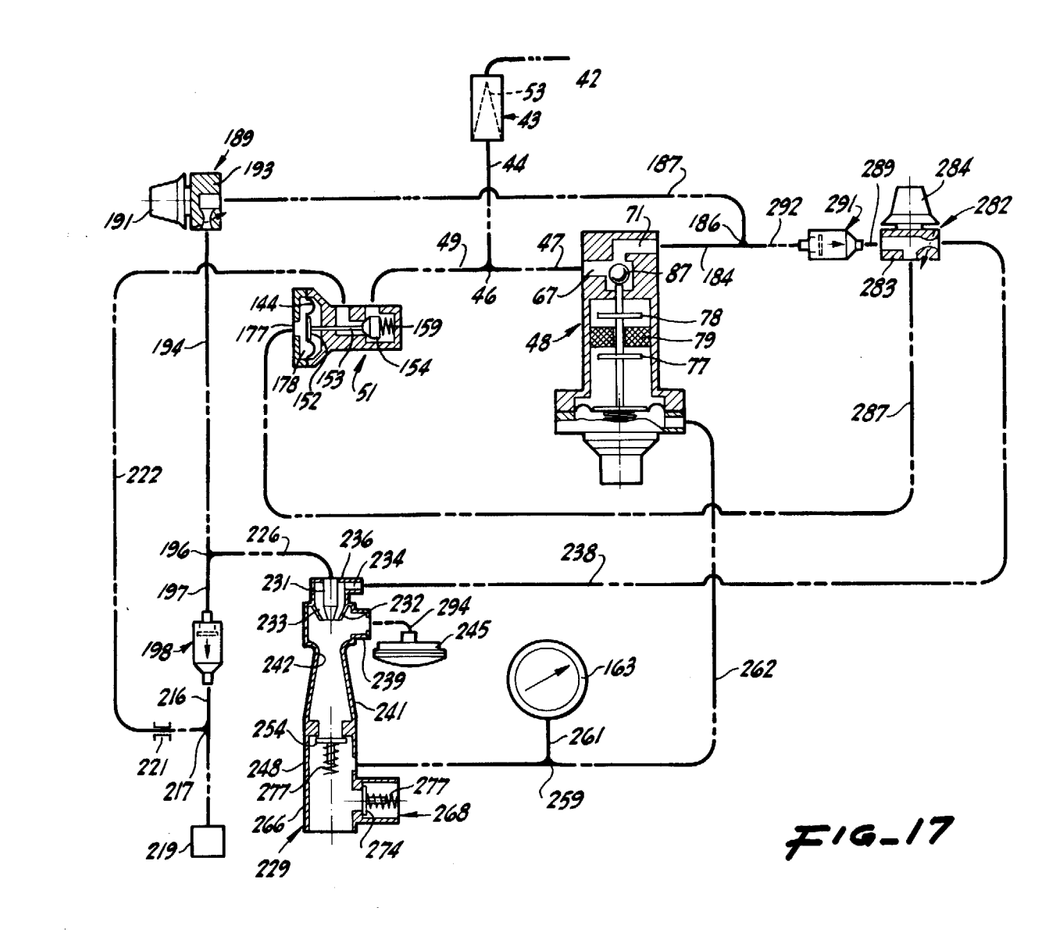
FIG. 17 is a flow diagram for the ventilator.

As shown in FIG. 13, the check valve assembly 198 consists of a central body 201 on which there is mounted a housing 202 both of which are formed of a suitable material such as plastic and are fastened together in a suitable manner such as by ultrasonic welding to provide a bubble tight seal. The central body 201 has a cylindrical portion 201a of reduced diameter as shown in FIG. 13. It is also provided with a flange 203 on the end of the portion 201a of reduced diameter. A passage or bore 207 is provided in the central body and extends longituidnally thereof through a stem-like portion 201b of the central body. The passage 207 empties into a passage 208 extending diametrically of the central body 201. The passage 208 is normally closed by a sleeve 209 formed of a suitable elastic material such as rubber which is slipped over the portion 201a and is retained thereon by the flange 203. It can be seen that if air is entering under pressure in the passage 207 in a direction indicated by the arrow that it can cause the elastic member 209 to expand and to permit the gas to escape into the housing 202 and to be discharged therefrom through a passage 211. When the air ceases to be applied under pressure through the passage 207, the elastic member will close the openings or passage 208 and prevent gas flow in an opposite direction.

Figure 4:
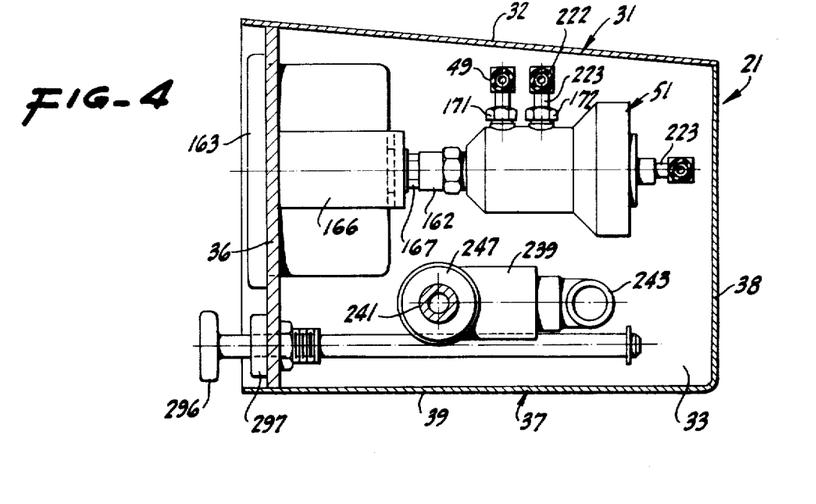
FIG. 4 is a cross-sectional view taken along the line 4—4 of FIG. 3.
Figure 5:
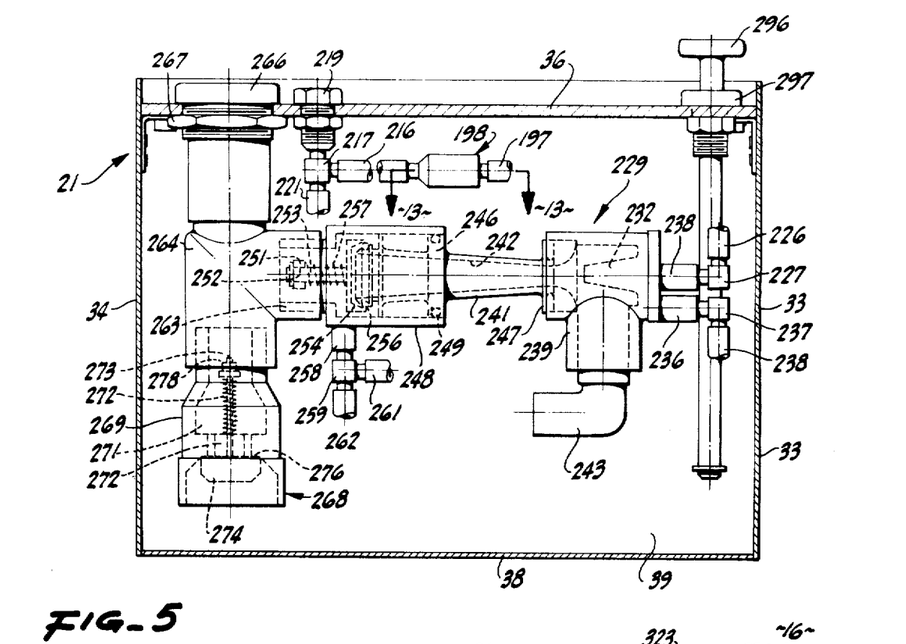
FIG. 5 is a cross-sectional view taken along the line 5—5 of FIG. 3.

The passage 111 is connected by a tube 216 to a tee 217. One end of the tube 216 is directly connected to the inspiratory power fitting 219 mounted on the front panel 36 which can be termed a second outlet. The other end of the tee 217 is connected through a member 221 providing a restricted orifice and then through a tube 222 which is connected by an elbow 223 which is mounted in the fitting 172. (See FIG. 4)

The end of the tee 196 is connected by tube 226 to a fitting 227 mounted in a boss 228 provided on a venturi assembly 229. The boss is provided with a main passage 231 which is centrally disposed in the nozzle 232 to provide a main venturi jet of gases. Additional passages 233 are provided in the nozzle 232 and are disposed around the centrally disposed passage 231 to provide secondary venturi jets. The passages 233 are in communication with a passage 234 provided in a boss 236. A fitting 237 is provided in the boss and is connected to a tube 238. The nozzle 232 is disposed in a T-shaped housing 239. One end of the housing 239 is threaded onto a venturi housing 241 which has a venturi passage 242 therein in communication with the jets of gas discharging from the passages 231 and 233 in the nozzle 232.

A fitting 243 is mounted in the other end of the housing 239 and is connected by a large tube 244 to an air inlet filter 245 mounted in the side wall 34. The venturi housing 241 is provided with first and second spaced parallel radially extending flanges 246 and 247 which are adapted to seat within a gate valve housing 248. An O-ring 249 is mounted in the flange 246 and establishes a seal between the venturi housing 241 and the gate valve housing 248.

The gate valve housing 248 is provided with an interior spider 251 which forms a centrally disposed hole 252 that receives the dish-shaped gate valve 254 which is adapted to engage the outer extremity of the venturi housing 248. An O-ring 256 is provided on the exterior of the venturi housing 241 to establish a good seal between the gate valve 254 and the venturi housing. Yieldable means is provided for urging the gate valve into engagement with the O-ring and consists of a helical spring 257 mounted on the stem 253 and having one end engaging the spider 251 and having the other end engaging the valve 254. The housing 248 is provided with a boss 258 which has a tee 259 mounted therein. One end of the tee 259 is connected by a tube 261 to the pressure manometer 168. The other end of the tee 259 is connected by a tube 262 to the sensing port 97 of the servo cartridge 48.

The gate valve housing 248 is provided with an outlet 263 which is connected to a tee 264. One end of the tee 264 is mounted in a breathing tube receptacle 266 which is mounted on the front panel 36 and which can be termed a first outlet. The receptacle 266 is contained within the front panel 36 by nut 267 which is threaded thereon. The other end of the tee 264 has a safety-blow off valve assembly 268 mounted therein.

The valve assembly 268 consists of a generally cylindrical housing 269 with a flow passage 271 therein. An apertured wall 272 is provided in the passage and has a valve stem 273 slidably mounted therein. A valve member 274 is carried by the valve stem and is adapted to engage a valve seat 276 which is formed on the housing and surrounds the passage 271. Means is provided for yieldably urging the valve member into engagement with the seat and consists of a spring 277 having one end engaging the wall 272 and having the other end engaging a nut 278 provided on the valve stem 273.

Figures 6, 15, 16:
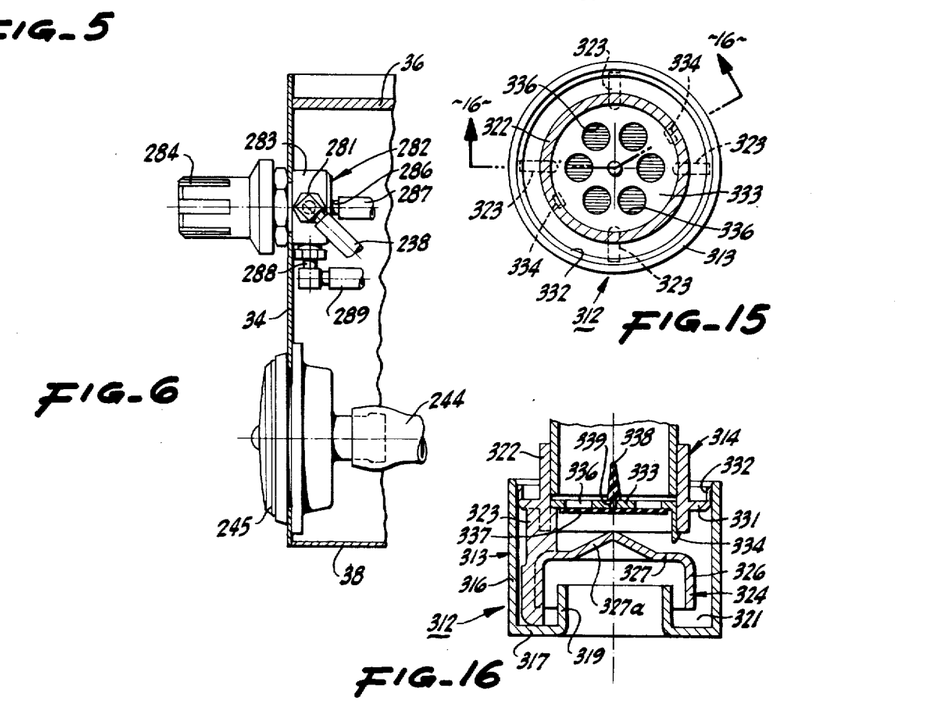
FIG. 6 is a partial cross-sectional view of the ventilator particularly showing the apneustic control valve assembly and an inlet filter.
FIG. 15 is a cross-sectional view taken along the line 15—15 of FIG. 1.
FIG. 16 is a cross-sectional view taken along the line 16—16 of FIG. 15.

The tube 238 is connected to a fitting 281 mounted in an apneustic plateau control valve assembly 282. The control valve assembly 282 is provided with a valve body 283 having a control knob 284 for adjusting the flow through the valve assembly. A fitting 286 is mounted on the valve assembly 282 and is connected to the tube 287 which is connected to a fitting (not shown) of the apneustic control valve assembly 51. The valve assembly 282 is provided with another fitting 288 (FIG. 6) which is connected by a tube 289 to a check valve assembly 291. The check valve assembly 291 is similar to the check valve assembly 198 and, therefore, will not be described in detail. The check valve assembly 291 is connected by a tube 292 to the tee 186.

A hanger rod 296 is slidably mounted in a fitting 297 provided in the front panel 36.

As shown in FIG. 1, a large breathing tube 301 is adapted to be mounted in the breathing tube receptacle 266. A small tube 302 is mounted in the inspiratory power control fitting 219. The other end of the large breathing tube 301 is connected to a fitting 303 which is connected into a nebulizer 304 of the type described in U.S. Pat. No. 3,172,406. The other end of the nebulizer 304 is connected to a tee 306 which has a patient adapter or mouthpiece 307 mounted in one end thereof and which has an exhaust valve assembly 308 mounted in the other end thereof. The small tube 302 is connected to a tee 309 which has one end mounted in the nebulizer 304. The other end of the tee 309 is connected by a tube 311 to the exhalation valve assembly 308. The exhalation valve assembly 308 is of a conventional type. A vapor trap assembly 312 is mounted on the exhalation valve assembly to collect moisture which has precipitated out of the airstream.

The vapor trap assembly 312 consists of an outer cup-like housing 313 in which there is removably mounted a gate valve and diffuser assembly 314. The housing 313 is generally cylindrical in shape and is provided with an upstanding cylindrical wall 316 with a bottom wall 317 formed integral therewith. A central opening 318 is provided in the bottom wall and is circumscribed by an upstanding lip or flange 319 so that there is provided an annular recess 321 between the upstanding flange 319 and the upstanding cylindrical wall 316. One end of the housing 313 is open and is adapted to receive the gate valve and diffuser assembly 314.

The gate valve and diffuser assembly 314 consists of a hollow cylindrical member 322 which is carried by a plurality of upstanding circumferentially spaced ribs or posts 323. The ribs or posts 323 are formed integral with a diffuser member 324. The diffuser member 324 is provided with a cylindrical wall 326 which is closed at its top by a transversely extending top wall 327. The top wall 327 is provided with a centrally disposed upwardly extending cone-shaped portion 327a which underlies the hollow cylindrical member 322. As will be noted, the lower extremities of the posts or ribs 323 extend below the bottom of the cylindrical wall 326 and are adapted to seat within the annular recess 321a in the housing 313. The annular rim 331 is formed integral with the hollow cylindrical member 322 and is provided with an upstanding flange 332 which is adapted to engage the inner surface of the cylindrical wal 316 of the housing 313 to frictionally retain the gate valve and diffuser assembly 314 within the housing 313. The lower extremity of the hollow cylindrical member 322 is spaced above the top wall 327.

A circular plate 333 is mounted within the hollow cylindrical member 322 and is seated upon the upper extremities of the ribs 323. The plate 323 is provided with downwardly depending ears 334 which are adapted to snap over the lower extremity of the hollow cylindrical member 322 to retain the plate 333 within the hollow cylindrical member 322. The plate 336 is formed with a plurality of openings 336 which are arranged in a circle. An umbrella-type flapper valve 337 formed of a suitable material such as a flexible plastic is provided to form a gate valve in conjunction with the openings 336. The flapper valve 337 is provided with a centrally disposed tit 338 which is mounted in a centrally disposed hole 339 provided in the plate 333 to retain the flapper valve 337 in engagement with the bottom side of the plate 333 to normally close the openings 336. The flapper valve 337 generally overlies the cone-shaped portion 337a so that when air passes through the openings 336 and pushes the flapper valve downwardly the air will be diffused outwardly over the diffuser member 324 and through the ribs and downwardly and then up and over the flange 319 and to the atmosphere through the opening 318.

Operation and use of the ventilator 20 may now be briefly described as follows. Let it be assumed that the ventilator 20 is to be utilized by a patient who is in a comfortable supine position or sitting erect in an armchair. The nebulizer 304 is filled with a suitable solution which is to be utilized by the patient and as may be prescribed by a physician. The tee 306 with the exhalation valve assembly 308 is then mounted on the nebulizer 304 with a mouthpiece or patient adapter 307. The water trap assembly 312 is mounted upon the exhalation valve assembly 308. The breathing tube 301 is placed in the breathing tube socket 266 and the tube 302 is mounted in the expiratory power fitting 219.

The starting effort for the patient is set by utilizing the control dial 116 which carries indicia ranging from 1 to 5. An appropriate setting is 2 which represents −2 cm of water. Next, the inspiratory positive pressure is set by utilizing the dial or knob 122. The dial or knob carries indicia ranging from 15 to 60 cm $H_2O$ and can be set within this range. For starting it should be set to 15. If desired a dual range can be provided with the one range of 15 to 60 p.s.i. as a therapy range and with another range of 15 to 100 p.s.i. as an intensive care range.

The flow rate is next adjusted by operating the knob 191 so that an arrow (not shown) carried by the knob is in the 12 o'clock position.

The manual control timer knob 131 is depressed inwardly and thereafter, the oxygen or air supply is turned on to supply oxygen or air or a mixture of the same through the tube 27 to the ventilator 20. The manual timer control knob 131 is then pulled out so that the ventilator is "on." There should be a dense flow of aerosol from the nebulizer 304. The manual timer control knob 131 is then pushed in to the ventilator "off" position. After this for a specific period of time (between 0.25 to 3 seconds) there should still be a flow of aerosol from the nebulizer 304. This is the apneustic flow time. The knob 284 is then rotated fully counterclockwise to the minimum period (0.25 second). The ventilator is then ready for use by the patient.

In operation of the ventilator, air from the source at suitable pressure such as 50 p.s.i. is supplied through the filter 43 and then through the tube 44 and the tubing 49 to the apneustic plateau cartridge 51 and also through the tube 47 to the servo cartridge 48.

Let it be assumed that the control knob 131 is moved to the left from the position shown in FIG. 7 to cause the master shaft 73 to be moved to the left which, in turn, causes movement of the servo plate 82 and the fitting 84 to the left. Movement of the fitting 84 to the left causes movement of the plunger 86 to the left to engage the ball 87 to move it out of engagement with the seat 88. In this position of the ball 87, source gases will flow around the ball and through the orifice or valve seat around the plunger 86 and out the outlet port 71. During this "on" or "open" period, the flow of the source gas around the ball literally spins the ball 87 on the end of the plunger 86 and serves to keep the ball free of microcontaminations such as could be carried by water. This flow through the port 71 can be identified as inspiratory flow gas.

Inspiratory flow gas is supplied through tube 184 and the tube 187 to the flow rate valve 189, then through the tube 194 and the tube 226 through the center venturi passage 231 of the venturi assembly 229. The jet of gases passing from the passage 231 in the nozzle 232 will pass down through the venturi 242 which will cause aspiration of additional gases which will be drawn in through the filter 245 and through the large bore tube 244 as shown particularly in FIG. 6. The gases which are supplied by the venturi passage 242 apply positive pressure to the gate valve 274 against the yieldable force of the spring 277 to open the gate valve and to permit the gases to be discharged through the receptacle 266 and thence through the large tube 301 through the nebulizer 304, the tee 306 and the mouthpiece 307 to the patient. At the same time, inspiratory gases are being supplied by the tube 197 to a check valve assembly 198 to the inspiratory power socket 219 provided on the front panel 36. The small tube 302 is connected to this inspiratory power socket and supplies inspiratory gases under pressure to the nebulizer 304 and to the exhalation valve assembly to maintain the same closed during the inhalation or inspiratory phase of the ventilator. The safety blow-off valve assembly 268 is provided to protect the patient from over-pressure as, for example, a pressure above 67 cm of water, to prevent damaging the patient's lungs.

As herein before pointed out, means is provided for sensing the pressure of the gases being supplied to the patient and consists of the manometer 168 which is connected to the outlet receptacle 266. It also is connected through the tube 262 to the sensing port 97 of the servo cartridge 48.

Inspiratory gas is also supplied through the tube 292 through a check valve assembly 291 through the apneustic control valve assembly 282 through tube 238 to the passage 234 provided in the venturi assembly 229. The passage 234 is connected to a plurality of passages 233 provided in the nozzle 232 to provide additional or secondary venturi jets of gas which are directed through the throat of the venturi assembly to augment the flow of gases through the venturi. The gas under pressure is also supplied from the apneustic control valve 282 through a tube 287 to the normally closed apneustic plateau cartridge 51 to move it to the open position. Additional inspiratory gases are supplied to the inspiratory power socket 219 through the orifice 271 at a fixed rate as determined by the size of the orifice 271. The orifice 271 is supplied with inspiratory gases from the tube 222 which is fed from the open apneustic plateau cartridge 51 which in turn is fed by the tube 49. These additional inspiratory gases augment the flow of gases through the nebulizer 304.

The initial flow of inspiratory gases during the inspiratory phase of the ventilator delivers inspiratory air into the distal airway or ducts of the patient's lungs. Automatic nebulization occurs during inspiratory phase because the inspiratory gases pass through the nebulizer 304. The rate of inspiratory flow determines the volume of inspiratory nebulization. As flow rate is increased, the pressure behind the primary jet of gases from the nozzle 232 increases causing an increased flow into the breathing circuit. In the present invention the basic inspiratory flow rate is supplemented or augmented by parallel flows of inspiratory gases one of which is through the apneustic plateau cartridge 51 and the other of which is through the apneustic control valve 282. The flow through the cartridge 51 which is fixed by the size of the orifice 271, continues throughout the inspiratory phase and for a period of time after the end of the inspiratory phase as determined by the setting of the apneustic control valve 282. Thus there is provided a minimum flow from the nebulizer regardless of the slowing of the inspiratory flow rate near the end of the inspiratory phase. In this manner it is possible to effectively double the volume of particulate delivery from the micronebulizer 304 during slow flow techniques.

From the foregoing it can be seen that a "topping low flow" is introduced into the patient's breathing circuit during the period of apneustic hold which is encountered after termination of the inspiratory phase. Decreasing the apneustic flow time increases the rate of flow of bleed down gases through the secondary venturi jets during the apneustic plateau and conversely increasing the apneustic flow time decreases the rate of flow of bleed down gases through the secondary venturi jets during the apneustic plateau. Also there is an analog tapering off of the rate of flow of the bleed down gases near the end of the apneustic plateau which creates a gradual pressure drop within the physiological system of the patient to prevent an abrupt rapid expiratory flow. These latter features are important because they make it easy to teach the patient how to use the ventilator to provide a satisfactory apneustic plateau.

With the present ventilator, a post-inspiratory apneustic plateau ranging from 0.25 to 3 seconds in duration can be provided by adjustment of the control knob 284 of the apneustic control valve 282. In this way, it is possible to further enhance the total inspiratory distribution of respiratory gases transporting topically active aerosols. By way of example, it has been found that during apneustic flow approximately 200 cc of inspiratory gas is delivered per second so that during a maximum 3 second apneustic plateau, as much as 600 cc of dense aerosol can be delivered to the patient's lungs. Thus, it can be seen that during the initial inspiratory flow the humidity deficits are resolved, whereas during apneustic flow a larger particle high volume aersol is delivered into the tracheobronchial tree to effectively enhance the mobilzation of retained tracheobronchial secretions.

When a certain pressure is reached in the lungs of the patient as measured by the manometer 168 and since through the tube 262 connected to the servo cartridge, the pressure present in the chamber 102 will cause movement of the diaphragm 94 and the master shaft 73 to the right as viewed in FIG. 7. This movement of the master shaft causes the plunger 86 to move to the right towards a closed position and permits the ball 87 to approach its orifice seat or valve seat. The size of the passage between the ball 87 and the orifice seat decreases to increase the flow velocity of the gases. This minimizes the tendency for the ball to fly off the seat during low flow when the plunger is withdrawn to the off position. To completely eliminate the possibility of a flying ball (during expected low flow conditions) causing an incompetent switch over (from the inspiratory to the expiratory phase), circumferentially spaced, longitudinally extending spoiler strips are formed in the cylindrical walls of the passage 68. These spoiler strips cause the ball to stall out on its orifice seat during low flow serving to further guarantee a competent closing. Since the plunger 86 is mechanically linked by the servo disc 82 to the master shaft 73, the plunger 86 is pulled to permit the ball 87 to move to a closed position and is pushed to move the ball from the closed position.

Opening and closing of the switch of which the ball 87 forms a part occurs at approximately the mid point of the master shaft travel. Over-travel in both the on and off directions accomodates master shaft travel between the magnetic on and off clutches as described.

At the servo cartridge 48 "off" position, the ball valve 87 is held in closed position by the pressure of the source gas which enters at inlet port 67 and passes into passage 68 and then pushes ball 87 against seat 88. The magnetic force of magnet 79 holds armature plate 77, which through shaft 73 and servo plate 82 keeps pin 86 away from ball 87. At the servo cartridge 48 "on" position, the magnet 79 holding armature plate 78, which through shaft 73 and servo plate 82 pushes pin 86 which holds ball 87 away from seat 88. Source gases are allowed to pass through from cavity 68 to outlet port 71. Magnetic fields are created by the fixed ring magnet 79. The strong front field is used to attract the large (pressure limiting) armature 78. The weaker back field of the magnet influences the smaller (starting effort) armature 77.

When beginning inspiratory break-away occurs within the servo cartridge 48 by reducing the pressure in the chamber 102, the starting effort armature 77 moves away from its magnetic field and the pressure limiting armature moves into its magnetic field under the influence of increasing magnetic force. The magnetic opening force is necessary to prevent a stall (peak starting effort sensitivity) against the piston effect created during opening of the ball valve. This is provided in the design of the servo cartridge by controlling the distance between the pressure limiting armature and its magnetic field to provide sufficient "pull-through" forces as servo plunger 86 contacts the ball during movement to the switch "on" position.

As the pressure limiting armature moves towards the front field of the magnet, the "pulling force" of the magnet pulls rapidly right. The opposite is true with the starting effort armature as it moves progressively out of the influence of the magnetic back field. Because of the proportionate increase and decrease of the distances as one armature approaches and the other departs its magnetic field, only one magnetic field can capture its armature at a time. This establishes the positive snap on-snap off function of the pneumatic ball valve.

The functions of the magnetically controlled valve are interfaced with the servo sensing diaphragm 94 which is capable of applying servoing forces to the master shaft 73 carrying the magnetic armatures 77 and 78. The diaphragm area is of sufficient size to override the magnetic "on-off" clutches at their maximum torques.

At the commencement of the inspiratory phase, the pressure inside the airways of the lung start to drop below ambient. This sub-ambient condition is transmitted through the sensing port 97 to the back side of the diaphragm 94 so that the diaphragm will apply force to move the master shaft 73 to the left as viewed in FIG. 7. This movement is resisted by the magnetic (starting effort) source supplied to the starting effort armature 77. As the physiological diaphragm of the patient continues to descend during the initial inspiratory phase, sub-ambient pressures acting against the servo diaphragm 94 increase until the ON servoing force supplied by the diaphragm 94 exceeds the opposing force supplied by the preset commanding magnetic off force set up by the starting effort armature 77. As soon as this occurs, the master shaft 73 will travel to the left causing the pneumatic ball valve 87 to open.

A controlled inspiratory flow of gas into the breathing circuit occurs as hereinbefore described. As the lungs of the patient gradually fill with the respiratory gases into the breathing circle connected to the patient, pressures within the physiological and mechanical ventilatory systems begin to rise. The previous pressure drop across the servo diaphragm favoring switching to the "on" position is now reversed and the pressure favoring switching to the "off" position is created. When sufficient pressure is supplied to the chamber 102 to create a force large enough to overcome the force applied by the pressure limiting armature 78, the master shaft 73 is shifted to the right as viewed in FIG. 7 so that the starting effort armature comes into control of the magnetic field supplied by the magnet 79. The servo cartridge 48 is switched to the opposite position by movement of the plunger 86 to the right and the ball valve 87 seats upon its valve seat to prevent further flow of source gases through the servo cartridge 48.

By adjustment of the armature 77 on the master shaft 73, it is possible to preselect a definite value of patient effort required to switch the ventilator on during mechanically assisted spontaneous breathing. In addition, it is possible to preselect a definite positive inspiratory pressure limit by adjusting the position of the armature 78. Positioning of the armatures 77 and 78 can be adjusted in relation to calibrated adjustable sensitivity and pressure control knobs 116 and 122, respectively. Calibration of the starting effort sensitivity is expressed in negative centimeters of H₂O and is indexed counterclockwise 1 to 5 and represents the pressure drop required in centimeters of H₂O during spontaneous inspiration to trigger the servo cartridge 48 to the "on" position for assisted mechanical respiration.

Pressurization of the chamber 178 occurs as soon as inspiratory gases are supplied through the apneustic plateau control valve 282 to the servo port 177 of the apneustic plateau cartridge 51. Diaphragm 147 is urged to the left to open the poppet valve 154 from a normally closed position. The apneustic plateau control cartridge utilizes a diaphragm seal in place of dynamic O-ring seals because of varying frictional loads associated with decreasing surface lubrication and service for O-ring seals.

As soon as the poppet valve 154 is moved to an open position, source gases are supplied through the inlet fitting 171 and out through the outlet fitting 172 through the tube 222 and then through the restricted orifice 221 to the receptacle 219.

When the servo cartridge 48 senses that a predetermined pressure has been reached in the patient's lungs, the servo cartridge is shifted from "on" to "off." This is accomplished because as the pressure builds up in the patient's lungs, it also builds up in the chamber 102 to cause the diaphragm 94 to apply a pressure to move the master shaft 73 to the right as viewed in FIG. 7 to move it to the "off" position in a manner hereinbefore described. As soon as this occurs, the ball valve 88 will seat on its seat to prevent further flow of source gas to the check valve 291 and to the apneustic plateau control valve 282. At the same time that the servo cartridge 48 moves to the "off" position, source gas under pressure is no longer supplied to the apneustic plateau cartridge.

At the time of sequencing of the servo cartridge 48, the apneustic plateau cartridge will still have a certain volume of gas in the chamber 178 which is at the pressure of the inlet source gas. This gas must be brought out through the line 287 through the apneustic plateau control valve 282 and through the tube 238 through the venturi assembly 229. The time required to bleed down this chamber 178 is determined by the adjustment of the knob 284 of the apneustic plateau control valve 282. Thus, source gas under the 50 p.s.i. pressure will be supplied through the tube 49, through the inlet fitting 171, through the outlet fitting 172 and through the tube 222, through the restricted orifice 221 to the receptacle 219 so that even after the servo cartridge 48 has servoed to the "off" position, source gas will be supplied to the breathing tube receptacle 219 and to the patient. At the same time, source gas under pressure will be supplied to the inspiratory power fitting 219. Thus, after the servo cartridge 48 has switched to the "off" position to end the inspiratory phase, there will still be a diminishing topping off or a supplemental flow of source gas through the secondary venturi jets 333 to the lungs of the patient as hereinbefore described.

It is only after sufficient gas has been bled out of the chamber 178 to permit the spring 159 to move the valve member 154 to a closed position that the flow of source gas to the patient ceases. At the same time, source gas under pressure is no longer supplied to the socket 219 and to the exhalation valve so that the exhalation valve can open and the patient can exhale through the exhalation valve.

The exhalation gases from the exhalation valve assembly 308 are exhausted through the vapor rap assembly 312. These exhalation gases must pass through the openings 336 and must urge the flapper valve 337 away from the openings to permit the exhalation gases to pass downwardly and outwardly over the diffuser member 324 and down past the ribs 323 and then upwardly over the flange 319 through the central opening 318 to the atmosphere. The flapper valve forces the patient to breathe or exhale against a graded positive pressure as for example 3 centimeters of water. As is well known to those skilled in the art, the use of means requiring the patient to exhale against a positive pressure is particularly efficacious with patients having obstructive pulmonary diseases. The flapper valve is of a type which serves to retard the flow of gases very little at peak flows of gases but does serve to retard the flow of gases at slow rates of flow. Thus it can be seen that the vapor trap assembly 312 does provide a retard function and in addition serves to collect vapors from the exhalation gases within the housing 313. The housing 313 can be readily removed from the gate valve and diffuser assembly 314 and emptied when necessary.

As soon as the expiratory phase has been completed, the patient will cause the sub-ambient condition to occur in the chamber 102 of the servo cartridge 48 to switch the servo cartridge 48 to the "on" position in the manner hereinbefore described to start another cycle.

From the foregoing, it can be seen that there has been provided a ventilator or respirator in which a topping low flow is introduced into the pulmonary structures of the patient during the period of apneustic hold at the end of the inspiratory phase. This topping low flow at the post inspiratory apneustic plateau can be from 0.25 to 3 seconds in duration and is particularly useful to permit topically active particles of aerosol to rain out in the pulmonary structures concommitant with increased diffusion and mechanical mixing of the expiratory gases in the lung of the patient. In addition, it can be seen that the ventilator which has been provided is of a construction which can be readily manufactured. Its construction is such that it is relatively simple to operate. It is also readily cleaned and maintained.

I claim:

1. In a servo controller for use in a ventilator having an inhalation phase and an exhalation phase in its operative cycle, a housing having an inlet and an outlet and a flow passage establishing communication between the inlet and the outlet, control valve means disposed within the housing and movable between open and closed positions to control the flow of gas from the inlet to the outlet of the housing, a master shaft mounted in the housing and coupled to the control valve means, magnetic means mounted within the housing for applying force to the master shaft, said magnetic means including first and second magnetic elements which are adjustable to apply varying amounts to force to the master shaft in opposite directions, and a compound knob arrangement mounted on one end of said housing and coupled to said magnetic elements to thereby vary the forces applied to the magnetic elements to the master shaft.

2. A servo controller as in claim 1 wherein said compound knob arrangement includes first and second knobs in which the first knob is utilized for controlling pressure and the second knob is utilized for controlling sensitivity.

3. A servo controller as in claim 1 of the type which is adapted to be mounted on a panel having an opening therein, said controller having means adapted to be secured to the front panel and wherein said compound knob arrangement is disposed on one side of the front panel.

* * * * *